United States Patent [19]
Davis et al.

[11] Patent Number: 6,074,413
[45] Date of Patent: *Jun. 13, 2000

[54] DISPOSABLE ELASTIC THERMAL BACK WRAP

[75] Inventors: Leane Kristine Davis, Milford; Ronald Dean Cramer; William Robert Ouellette, both of Cincinnati, all of Ohio; Dawn Michele Kimble, Reisterstown, Md.; Amy Michelle Martini, Cincinnatti, Ohio

[73] Assignee: The Procter & Gamble Company, Cincinnati, Ohio

[ * ] Notice: This patent is subject to a terminal disclaimer.

[21] Appl. No.: 09/082,348

[22] Filed: May 20, 1998

Related U.S. Application Data

[63] Continuation-in-part of application No. 08/984,365, Dec. 3, 1997, abandoned, which is a continuation-in-part of application No. 08/777,830, Dec. 31, 1996, Pat. No. 5,925,072.

[51] Int. Cl.$^7$ .................................................... A61F 7/00
[52] U.S. Cl. .......................... 607/108; 607/112; 607/114
[58] Field of Search ........................... 607/108–112, 114; 165/46; 126/204; 602/2; 62/4

[56] References Cited

U.S. PATENT DOCUMENTS

| | | | |
|---|---|---|---|
| Re. 32,026 | 11/1985 | Yamashita et al. | 126/263 |
| 1,491,539 | 4/1924 | Kirschmann . | |
| 2,547,886 | 4/1951 | Poux | 62/1 |
| 2,562,121 | 7/1951 | Poux | 150/2.2 |
| 2,602,302 | 7/1952 | Poux | 62/1 |
| 3,463,161 | 8/1969 | Andrassy | 128/402 |
| 3,900,035 | 8/1975 | Welch et al. | 128/402 |
| 3,943,912 | 3/1976 | Nakayama | 128/1.3 |
| 4,095,583 | 6/1978 | Petersen et al. | 126/263 |
| 4,205,685 | 6/1980 | Yoshida et al. | 128/399 |
| 4,255,157 | 3/1981 | Yamaguchi et al. | 44/3 C |
| 4,268,272 | 5/1981 | Taura | 44/3 R |
| 4,282,005 | 8/1981 | Sato et al. | 44/3 R |
| 4,366,804 | 1/1983 | Abe | 126/263 |
| 4,470,417 | 9/1984 | Gruber | 128/402 |
| 4,516,564 | 5/1985 | Koiso et al. | 126/263 |
| 4,575,097 | 3/1986 | Brannigan et al. | 128/402 |
| 4,586,506 | 5/1986 | Nangle | 128/403 |
| 4,649,895 | 3/1987 | Yasuki et al. | 126/263 |
| 4,688,572 | 8/1987 | Hubbard et al. | 128/402 |

(List continued on next page.)

FOREIGN PATENT DOCUMENTS

| | | | |
|---|---|---|---|
| 0 014 300 A1 | 8/1980 | European Pat. Off. | A61F 7/00 |
| 0 370 600 A1 | 7/1989 | European Pat. Off. | F24J 1/00 |
| 160443 | 9/1983 | India | C09K 3/02 |
| 56-145846 | 11/1981 | Japan | A61F 7/03 |
| 57-170252 | 10/1982 | Japan | A61F 7/03 |
| 58-37075 | 3/1983 | Japan | C09K 5/00 |
| 3-100090 | 4/1991 | Japan | C09K 5/00 |
| 5-3171388 | 12/1993 | Japan | A47J 36/28 |
| 6-1969 | 1/1994 | Japan | C09K 5/00 |
| 6-315498 | 11/1994 | Japan | A61F 7/08 |
| 6-343658 | 12/1994 | Japan | A61F 7/08 |
| 7-67907 | 3/1995 | Japan | A61F 7/08 |
| 7-124192 | 5/1995 | Japan | A61F 7/08 |
| 7-49042 | 5/1995 | Japan | A61F 7/08 |
| 7-194641 | 8/1995 | Japan | A61F 7/08 |
| 7-194642 | 8/1995 | Japan | A61F 7/08 |
| 8-98856 | 4/1996 | Japan | A61F 7/08 |
| 8-126656 | 5/1996 | Japan | A61F 7/08 |
| 2 205 496 | 12/1988 | United Kingdom | A61F 7/03 |
| WO 94/00087 | 1/1994 | WIPO | A61F 7/00 |
| WO 94/12125 | 6/1994 | WIPO | A61F 5/02 |

*Primary Examiner*—Max Hindenburg
*Assistant Examiner*—Ryan Carter
*Attorney, Agent, or Firm*—Loy M. White; Douglas C. Mohl; T. David Reed

[57] ABSTRACT

The present invention relates to disposable thermal back wraps having one or more thermal packs comprising a plurality of heat cells, wherein heat is applied to specific areas of the user's back, for pain relief. More particularly, the present invention relates to disposable elastic thermal back wraps having good conformity to user's back which provides consistent, convenient and comfortable heat application.

54 Claims, 2 Drawing Sheets

U.S. PATENT DOCUMENTS

| | | | |
|---|---|---|---|
| 4,753,241 | 6/1988 | Brannigan et al. | 128/380 |
| 4,756,299 | 7/1988 | Podella | 126/263 |
| 4,860,748 | 8/1989 | Chiurco et al. | 128/399 |
| 4,886,063 | 12/1989 | Crews | 128/403 |
| 4,925,743 | 5/1990 | Ikeda et al. | 428/702 |
| 5,000,176 | 3/1991 | Daniel | 128/402 |
| 5,025,777 | 6/1991 | Hardwick | 126/263 |
| 5,046,479 | 9/1991 | Usui | 126/204 |
| 5,062,414 | 11/1991 | Grim | 128/68.1 |
| 5,072,598 | 12/1991 | Dibrell | 62/259.3 |
| 5,125,392 | 6/1992 | Hardwick | 126/263 |
| 5,148,804 | 9/1992 | Hill et al. | 128/402 |
| 5,179,942 | 1/1993 | Drulias et al. | 128/101.1 |
| 5,179,944 | 1/1993 | McSymytz | 128/403 |
| 5,190,033 | 3/1993 | Johnson | 128/403 |
| 5,233,981 | 8/1993 | Miyashita | 607/114 |
| 5,342,412 | 8/1994 | Ueki | 607/114 |
| 5,366,492 | 11/1994 | Ueki | 607/114 |
| 5,378,225 | 1/1995 | Chatman, Jr. et al. | 602/19 |
| 5,395,399 | 3/1995 | Rosenwald | 107/108 |
| 5,398,667 | 3/1995 | Witt | 126/263 |
| 5,399,150 | 3/1995 | Saunders | 602/19 |
| 5,405,671 | 4/1995 | Kamin et al. | 428/69 |
| 5,450,858 | 9/1995 | Zablotsky et al. | 128/876 |
| 5,484,366 | 1/1996 | Wilkinson | 482/105 |
| 5,496,357 | 3/1996 | Jensen et al. | 607/108 |
| 5,496,358 | 3/1996 | Rosenwald | 607/108 |
| 5,534,021 | 7/1996 | Dvoretzky et al. | 607/112 |
| 5,605,144 | 2/1997 | Simmons et al. | 126/204 |
| 5,925,072 | 7/1999 | Cramer et al. | 607/108 |

Fig. 1

DISPOSABLE ELASTIC THERMAL BACK WRAP

CROSS REFERENCE TO RELATED APPLICATION

This application is a continuation-in-part of application Ser. No. 08/984,365, filed Dec. 3, 1997, now abandoned which is a continuation-in-part of application Ser. No. 08/777,830, filed Dec. 31, 1996 U.S. Pat. No. 5,925,072.

TECHNICAL FIELD

The present invention relates to disposable thermal back wraps having one or more thermal packs comprising a plurality of heat cells, wherein heat energy is applied to specific areas of the user's back. More particularly, the present invention relates to disposable elastic thermal back wraps having good conformity to user's back which provides consistent, convenient and comfortable heat application.

BACKGROUND OF THE INVENTION

A common method of treating acute, recurrent, and/or chronic pain is by the topical application of heat to the afflicted area. Such heat treatments are used as a means of therapy for conditions which include aches, stiffness in muscles and joints, nerve pain, rheumatism and the like. Typically, the method for relieving pain using heat treatments has been to topically apply a relatively high heat, i.e., greater than about 40° C., for a short period of time, i.e., from about twenty minutes to about one hour.

Back pain is one of the most common complaints found in modern society. Heating pads and elastic compression bands are common devices used to relieve back pain. More recently, combinations of elastic wraps and heating pads have been available. Many of these combination devices, however, utilize hot water bottles, hot packs, and the like, which are reusable via the replenishment of thermal energy to the contents, including water and/or microwaveable gels, of such devices. Many of these current heating devices which require the thermal source to be replenished are inconvenient to use on a regular and extended basis. Further, the heat energy may not be immediately available when needed or released in a controllable manner. That is, many of these thermal units or devices do not provide long lasting heat and also do not maintain a consistent temperature over long periods of time. Proper positioning of the thermal energy also may not be maintainable during use. The beneficial therapeutic effects from this administration of heat diminish after the heat source is removed.

The present inventors, however, have discovered that maintaining a sustained skin temperature of from about 32° C. to about 50° C., preferably from about 32° C. to about 45° C., more preferably from about 32° C. to about 42° C., most preferably from about 32° C. to about 39° C., still most preferably from about 32° C. to about 37° C., for a period of from about twenty seconds to about twenty-four hours, preferably from about twenty minutes to about twenty hours, more preferably from about four hours to about sixteen hours, most preferably from about eight hours to about twelve hours, wherein the maximum skin temperature and the length of time of maintaining the skin temperature at the maximum skin temperature may be appropriately selected by a person needing such treatment, such that the desired therapeutic benefits are achieved without any adverse events, such as skin burns which may be incurred by using a high temperature for a long period of time, substantially relieves acute, recurrent, and/or chronic back pain, including skeletal, muscular, and/or referred back pain, of a person having such pain.

The present inventors have further discovered that preferably maintaining a sustained skin temperature of from about 32° C. to about 43° C., preferably from about 32° C. to about 42° C., more preferably from about 32° C. to about 41° C., most preferably from about 32° C. to about 39° C., still most preferably from about 32° C. to about 37° C., for a time period of greater than about 1 hour, preferably greater than about 4 hours, more preferably greater than about 8 hours, even more preferably greater than about 16 hours, most preferably about 24 hours, substantially relieves acute, recurrent, and/or chronic back pain, including skeletal, muscular, and/or referred back pain, of a person having such pain and substantially prolongs relief even after the heat source is removed from the afflicted body part.

Disposable heat packs based on iron oxidation, such as those described in U.S. Pat. Nos. 4,366,804, 4,649,895, 5,046,479 and Re. 32,026, are known. However, such devices have proven not totally satisfactory because many of these devices are bulky, cannot maintain a consistent and controlled temperature, have difficulty staying in place during use, and/or have unsatisfactory physical dimensions which hinder their effectiveness. Specifically, such devices cannot be easily incorporated into wraps which can comfortably conform to various body contours and hence deliver inconsistent, inconvenient and/or uncomfortable heat application to the body.

The present inventors have developed disposable elastic thermal back wraps which provide both compression and thermal energy in a controlled and sustainable manner. These wraps comprise one or more thermal packs having a unified structure, wherein each thermal pack comprises at least one continuous layer, preferably of a semirigid material, which is semirigid in specific areas of the thermal pack, yet which softens in between such areas when heated during use, most preferably comprising a coextruded material of polypropylene and ethylene vinyl acetate (EVA). The thermal pack or packs also comprise a plurality of individual heat cells, which typically comprise an exothermic composition, preferably comprising a specific iron oxidation chemistry, and having specific physical dimensions and fill characteristics, spaced apart and fixed within or to the unified structure of the thermal pack. Active heat cells, that is, heat cells having a temperature of about 35° C. or greater, preferably soften narrow portions of the continuous layer or layers of semirigid material immediately surrounding the heat cells. Any remaining portions of the continuous layer or layers which surround the softened portions preferably remain more rigid. The narrow, softened portions act as hinges between the heat cells and between any remaining, cooler, more rigid portions, bending preferentially more than either the heat cells or more rigid portions. This results in thermal packs which possess sufficient rigidity to maintain structural support of the heat cells, to prevent unacceptable stretching of structures of the continuous layer or layers during processing or use, and to deter easy access to heat cell contents, while still maintaining good overall drape characteristics when heated. The thermal pack or packs, when incorporated into the back wraps of the present invention, provide efficient and effective heat coverage by having excellent conformity with the user's back.

The present inventors have also discovered that it may be desirable to selectively place heat cells, in the thermal pack or packs when incorporated into the back wraps of the present invention, into positions fixed within or to the unified structure of the thermal pack, relative to each other which are sufficiently close so as to block some or all possible axes, which otherwise would have passed uninterrupted between the heat cells, through the thermal pack, or select regions thereof, to minimize or eliminate undesirable, uninterrupted fold lines, and/or to increase the structural support that the heat cell matrix imparts to the thermal pack. That is, placement of the heat cells into positions relative to each other which are sufficiently close to block some or all possible axes which would otherwise have passed uninterrupted, between the heat cells, causes the thermal packs to fold along a multiplicity of short interconnected fold lines oriented in a number of different directions relative to each other. Folding along a multiplicity of interconnected fold lines results in good overall drape characteristics.

It is therefore an object of the present invention to provide disposable elastic back wraps which comprise one or more thermal packs, comprising a unified structure having at least one continuous layer, preferably of a semirigid material which has different stiffness characteristics over a range of temperatures, and a plurality of individual heat cells, which provide a controlled and sustained temperature and which reach their operating temperature range relatively quickly. The heat cells are spaced apart and fixed within or to the unified structure of the thermal pack.

It is also an object of the present invention to provide disposable thermal back wraps having good overall drapability while maintaining sufficient rigidity to maintain structural support of the heat cells and to prevent unacceptable stretching of the continuous layer or layers during processing or use.

It is a further object of the present invention to provide disposable elastic thermal back wraps which can be worn under outer clothing with minimal visibility, which provide consistent, convenient and comfortable heat application and deterring easy access to heat cell contents.

It is a still further object of the present invention to provide methods of treating acute, recurrent, and/or chronic back pain, including skeletal, muscular, and/or referred back pain, of a person suffering from such pain, by maintaining a sustained skin temperature of from about 32° C. to about 50° C. for a period of time of from about twenty seconds to about twenty-four hours, preferably by maintaining a skin temperature of from about 32° C. to about 43° C. for a time period of greater than about 1 hour to provide prolonged relief from such pain.

These objectives and additional objectives will become readily apparent from the detailed description which follows.

SUMMARY OF THE INVENTION

The disposable elastic thermal back wraps of the present invention comprise at least one substantially rectangular piece of flexible material having an outer surface, a body-facing side, a first end, a second end, and an elastic portion between first end and second end, stretchable along a longitudinal axis of the flexible material. The flexible material has a length great enough to encircle a user's torso such that the first and second ends overlap. The flexible material has a reclosable fastening means, preferably a hook and loop fastening system, for attaching the first end of the flexible material near the second end of the flexible material, in order to hold the finished disposable elastic thermal back wrap around the user's torso.

The disposable elastic thermal back wraps of the present invention further comprise one or more thermal packs. The thermal pack or packs comprise a unified structure having at least one continuous layer of a material, which is preferably semirigid at a temperature of about 25° C., having a tensile strength of about 0.7 g/mm$^2$ or greater, and at least two-dimensional drape, and which is substantially less rigid at a temperature of 35° C. or greater, having a tensile strength substantially less than the tensile strength of the material at about 25° C.

The continuous layer or layers of the present invention preferably comprise a coextruded material, more preferably a coextruded material comprising polypropylene, most preferably a coextruded material wherein a first side comprises polypropylene and a second side comprises a tie-layer of a low melt temperature copolymer, preferably EVA.

The thermal pack or packs further comprise a plurality of individual heat cells, which preferably comprise a mixture of powdered iron, powdered carbon, water, and salt, which when exposed to oxygen, provide a controlled and sustained temperature and which reach their operating temperature range quickly. The heat cells are spaced apart and fixed within or to the unified structure of the thermal pack. Preferably the heat cells are placed into positions fixed within or to the unified structure of the thermal pack, relative to each other and sufficiently close so that some or all of the possible axes that would otherwise pass uninterrupted between the heat cells are blocked by the heat cells to cause the thermal packs to fold along a multiplicity of short interconnected fold lines.

The fastening means has a plurality of hook members which engage loop fibers of a landing zone attached to the piece of flexible material in order to adjust the wrap to a variety of user torso sizes and to attain a comfortable level of elastic tension.

The present invention still further comprises methods of treating acute, recurrent, and/or chronic back pain, including skeletal, muscular, and/or referred back pain, of a person having such pain, by applying the disposable elastic thermal back wraps of the present invention to the back of a person having such pain, to maintain a sustained skin temperature of from about 32° C. to about 50° C. for a period of time of from about twenty seconds to about twenty-four hours, preferably to maintain a skin temperature of from about 32° C. to about 43° C. for a time period of greater than about 1 hour, to provide prolonged relief from such pain.

All percentages and ratios used herein are by weight of the total composition, and all measurements made at 25° C., unless otherwise specified.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify identical elements and wherein:

DETAILED DESCRIPTION OF THE INVENTION

The disposable elastic thermal back wraps of the present invention comprise one or more thermal packs having at least one continuous layer of a material which preferably exhibits specific thermophysical properties, and a plurality of individual heat cells which preferably comprise an exothermic composition, spaced apart and fixed within or to the structure of the disposable thermal pack.

The material of the at least one continuous layer is preferably semirigid when at room temperature, i.e., about 25° C., or below, but softens and becomes substantially less rigid when heated to about 35° C., or greater. Therefore, when heat cells, which are fixed within or to the unified structure of the thermal packs, are active, that is at a heat cell temperature of about 35° C. or greater, the narrow portion of the continuous layer or layers of material immediately surrounding each heat cell preferably softens and acts as a hinge between the heat cells and between any remaining, more rigid portions of the continuous layer or layers, bending preferentially more than either the heat cells or cooler, more rigid portions. This results in thermal packs which possess sufficient rigidity to maintain structural support of the heat cells and prevent unacceptable stretching of structures of the continuous layer or layers during processing or use, while still maintaining good overall drape characteristics when heated. The disposable elastic thermal back wraps of the present invention, provide consistent, convenient, and comfortable heat application, and an excellent conformity to the user's body, while retaining sufficient rigidity to deter easy access to heat cell contents.

"Disposable", as used herein, means that, while the thermal back wraps of the present invention may be stored in a resealable, substantially air-impermeable container and reapplied to the user's body as often as required for the relief of pain, they are intended to be thrown away, i. e., deposited in a suitable trash receptacle, after the heat source, i. e., the heat cell(s) or thermal pack(s), has been fully expended.

"Heat cells", as used herein, means a unified structure, comprising an exothermic composition, preferably a specific iron oxidation chemistry, enclosed within two layers, wherein at least one layer may be oxygen permeable, capable of providing long lasting heat generation with improved temperature control, and having specific physical dimensions and fill characteristics. These heat cells can be used as individual heating units, or in a thermal pack comprising a plurality of individual heat cells which can also be easily incorporated into disposable body wraps, pads, and the like. Thermal packs and body wraps incorporating thermal packs adapt to a wide variety of body contours, thus providing consistent, convenient, and comfortable heat application.

"Plurality of heat cells", as used herein, means more than one, preferably more than two, more preferably more than three, most preferably more than four, heat cells.

"Agglomerated pre-compaction composition", as used herein, means the mixture of dry powdered ingredients, comprising iron powder, carbonaceous powder, metal salt (s), water-holding agent(s), agglomeration aid(s), and dry binder(s) prior to direct compaction.

"Direct compaction", as used herein, means a dry powder mixture is blended, compressed, and formed into pellets, tablets, or slugs without the use of typical wet binders/solutions to adhere the particulate(s) together. Alternatively, the dry powder mixture is blended and roll compacted or slugged, followed by milling and screening, creating directly compacted granules. Direct compaction may also be known as dry compaction.

"Heating element(s)", as used herein, means the exothermic, direct compacted, dry agglomerated pre-compaction composition formed into compaction articles, such as granules, pellets, slugs, and/or tablets capable of generating heat, after an aqueous solution such as water or brine (salt solution) is added, by the exothermic oxidation reaction of iron. Agglomeration granules of said agglomerated pre-compaction composition are also included as heating elements herein.

The "fill volume", as used herein, means the volume of the particulate composition or the compacted, water-swelled, heating element in the filled heat cell. The "void volume", as used herein, means the volume of the cell left unfilled by the particulate composition or the compacted, water-swelled, heating element in a finished heat cell, not including the unfilled space within a tablet comprising a hole or reservoir, in a finished heat cell, measured without differential pressure in the heat cell and without additional stretching or deformation of the substrate material. The "cell volume", as used herein, means the fill volume plus the void volume of the heat cell.

"Continuous layer or layers", as used herein, means one or more layers of a material which may be uninterrupted or partially, but not completely, interrupted by another material, holes, perforations, and the like, across its length and/or width.

"Rigid", as used herein, means the property of a material wherein the material may be flexible, yet is substantially stiff and unyielding, and which does not form fold lines in response to gravitational pull or other modest forces.

"Semirigid material", as used herein, means a material which is rigid to some degree or in some parts, i. e., having at least two-dimensional drape at a temperature of about 25° C., and exhibits a toughness to maintain structural support of the heat cells in an unsupported format, and/or to prevent unacceptable stretching of structures of the material during processing or use, while still maintaining good overall drape characteristics when heated, and/or retaining sufficient rigidity to deter easy access to deter easy access to heat cell contents.

"Two dimensional drape", as used herein, means drape which occurs across a continuous layer or layers, across a thermal pack, or across a select region of a layer or layers, or thermal pack, exclusively along one axis, i.e., one fold line forms, at the expense of other fold lines in response to gravitational pull or other modest forces.

"Three dimensional drape", as used herein, means drape which simultaneously occurs across a continuous layer or layers, across a thermal pack, or across a select region of a layer or layers, or thermal pack, along two or more axes, i. e., two or more fold lines form, in response to gravitational pull or other modest forces.

"Fold lines", as used herein, means the line along which a material forms a temporary or permanent crease, ridge, or crest in response to gravitational pull or other modest forces.

It is understood that the disposable elastic thermal back wraps of the present invention may contain one or more thermal packs. However, for clarity, a disposable elastic thermal back wrap comprising a single thermal pack will be described herein.

Figure 1:
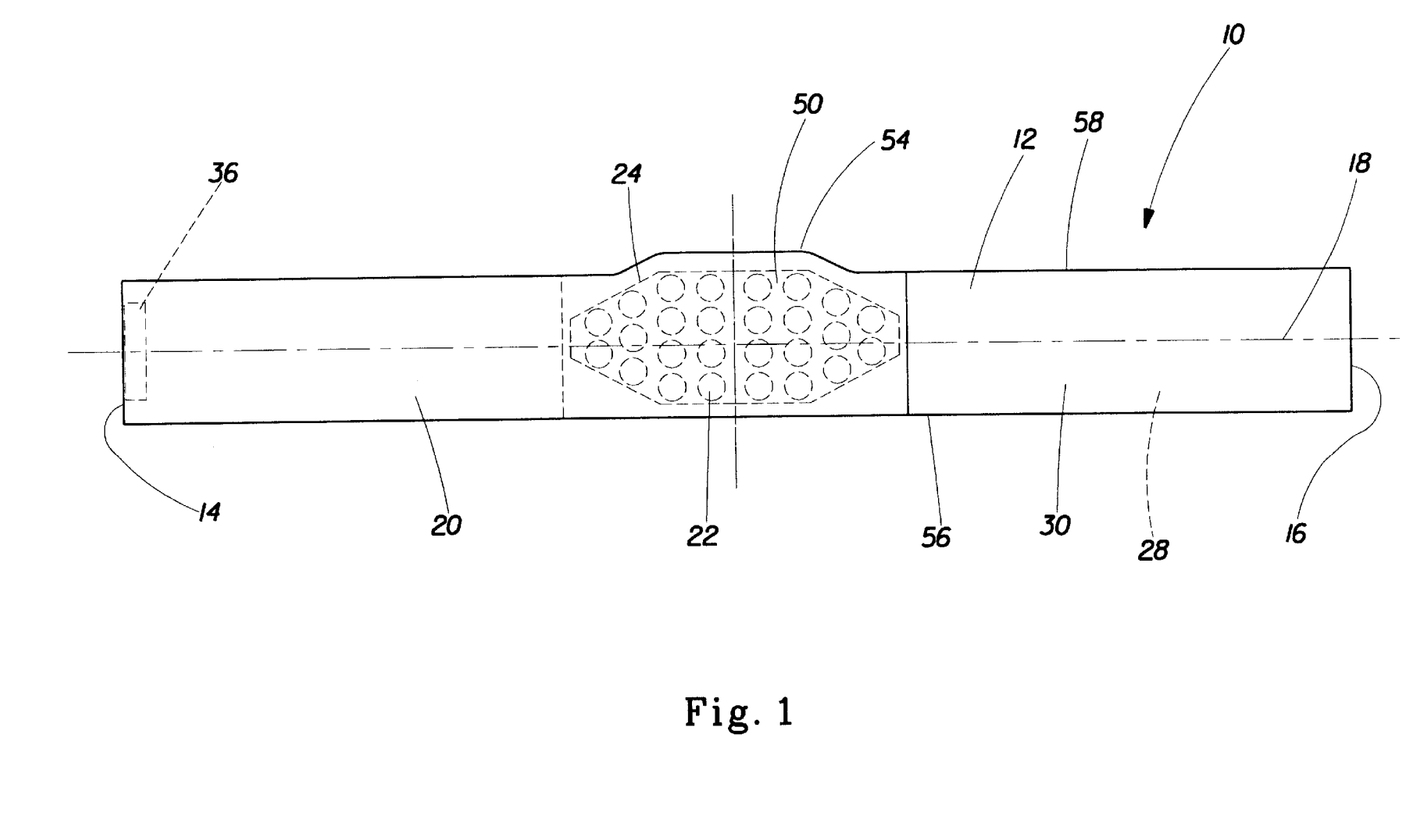
FIG. 1 is a top plan view of a preferred embodiment of the disposable elastic back wrap of the present invention, showing the preferred pattern of thermal pack(s) and/or heat cells embedded therein.
Figures 2, 2A, 2B:
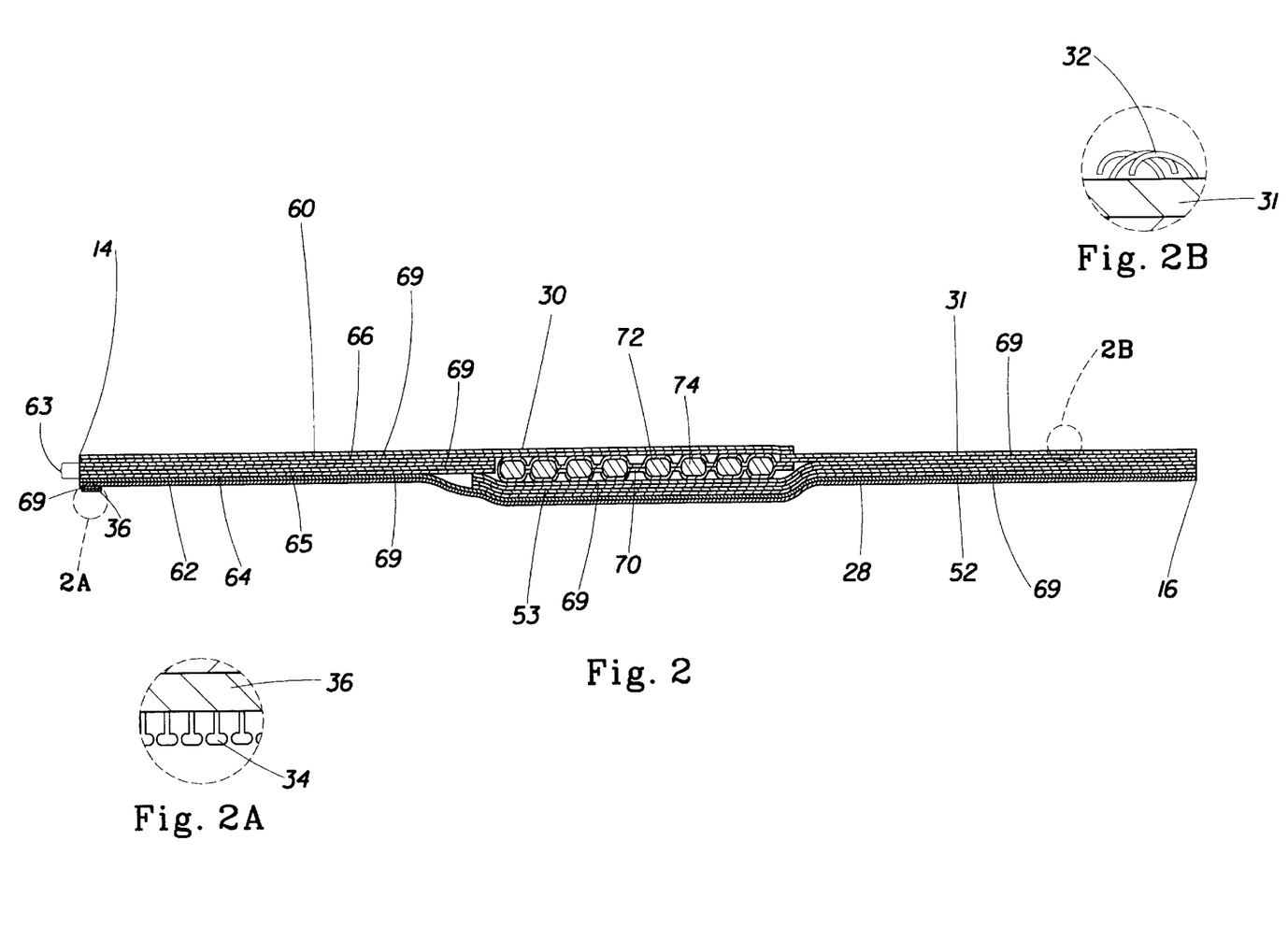
FIG. 2 is a sectioned side elevation view of FIG. 1.

Referring now to the drawings, and more particularly to FIGS. 1 and 2, there is shown a preferred embodiment of the present invention, which provides a disposable elastic thermal back wrap, generally indicated as 10. Elastic back wrap 10 comprises at least one substantially rectangular piece of flexible material 12 having a longitudinal axis 18. Flexible material 12 has a first end 14 and a second end 16 and an elastic portion 20 therebetween capable of being stretched along longitudinal axis 18. Flexible material 12 also has a first edge 56 and an opposing second edge 58, both first edge 56 and second edge 58 extending from first end 14 to second end 16. Flexible material 12 further has a length, as measured in a direction parallel to longitudinal axis 18, from first end 14 to second end 16, when in a relaxed or stretched state, which is great enough to encircle a user's torso (i. e., thorax, waist, hips), such that first end 14 overlaps second end 16 when wrap 10 is positioned around a user. Flexible material 12 of back wrap 10 has a body-facing side 28 and a continuous outer surface 30, both body-facing side 28 and outer surface 30 extending from first end 14 to second end 16.

As used herein, "elastic" refers to that property of a material whereby the material, when subjected to a tensile force, will stretch or expand in the direction of the force and will essentially return to its original untensioned dimension upon removal of the force. More specifically, the term "elastic" is intended to mean a directional property wherein an element or structure has a recovery to within about 10% of its original length $L_o$ after being subjected to a percent strain $\epsilon\%$ of greater than 50%. As used herein, percent strain $\epsilon\%$ is defined as:

$$\epsilon\% = [(L_f - L_o)/L_o]*100$$

Where $L_f$=Elongated Length
$L_o$=Original Length

For consistency and comparison, the recovery of an element or structure is preferably measured 30 seconds after release from its elongated length $L_f$. All other elements or structures will be considered inelastic if the element or structure does not recover to within about 10% of its original length $L_o$ within 30 seconds after being released from a percent strain $\epsilon\%$ of 50%. Inelastic elements or structures would also include elements or structures which fracture and/or permanently/plastically deform when subjected to a percent strain $\epsilon\%$ of 50%.

Preferably, outer surface 30 of wrap 10 contains a landing zone 31. Landing zone 31 may be coextensive outer surface 30 from first end 14 to second end 16 or alternatively, may extend from second end 16 to about interfacial line 55. Landing zone 31 comprises a plurality of loop fibers 32 disposed along the extent of landing zone 31 in the direction of longitudinal axis 18. The plurality of loop fibers 32 of landing zone 31, serve as the loop member of a reclosable hook and loop fastening system. As used herein the term "reclosable", means the property of a fastening system which provides for initial closing of the fastening system, a subsequent opening of the fastening system, followed by at least one additional closing of the same fastening system. The subsequent closing of the fastening system may either return the closure to the original position or it may result in a repositioning of the closure from the initial configuration. Body-facing side 28 of flexible material 12 comprises hook member 36, having a plurality of hooks 34, which is permanently attached to body-facing side 28 adjacent first end 14. As used herein, the term "permanently attached", means the joining of two or more elements which remain joined during their intended use. Hook member 36 on body-facing side 28, together with plurality of loop fibers 32 on landing zone 31 on outer surface 30, provide a reclosable hook and loop fastening system for securing first end 14 of flexible material 12 to outer surface 30 of flexible material 12 to hold wrap 10 in position when flexible material 12 is positioned around the wearer's torso, with first end 14 overlapping second end 16. This overlapping of flexible material 12 positions hook member 36 on body-facing side 28 over loop fibers 32 of landing zone 31 on outer surface 30. Since loop fibers 32 are disposed continuously along landing zone 31, hook member 36 may be engaged with loop fibers 32 at any position along landing zone 31 of continuous outer surface 30 of flexible material 12.

Alternatively, wrap 10 may comprise a two part hook and loop fastening system. That is, outer surface 30 may comprise a plurality of loop fibers 32. Similarly, body-facing side 28 may also comprise a plurality of loop fibers 32. The plurality of loop fibers 32 serve as one-half of a reclosable hook and loop fastening system. Body-facing surface 28 may comprise hook member 36, having a plurality of hooks 34, which is permanently attached to body-facing surface 28 near first end 14. Similarly, outer surface 30 may comprise hook member 36, having a plurality of hooks 34, which is permanently attached to outer surface 30 near second end 16. The plurality of hooks on hook members 36 serves as the second half of a reclosable hook and loop fastening system. Upon application of wrap 10, first end 14 encircles the user's torso, overlapping second end 16 such that, hook members 36 on outer surface 30 near second end 16 engage loop fibers 32 on body-facing surface 28. Engagement of hook members 36 with loop fibers 32 forms the first part of the twopart hook and loop fastening system. Continuing the application, hook members 36 on the body-facing surface 28 near first end 14 are placed in contact with loop fibers 32 of outer surface 30 forming the second part of a two-part hook and loop fastening system.

Hooks 34 may be any number of styles, shapes, and/or densities depending upon the use. Hooks 34 may be bent shafts, mushroom capped, harpoon-shaped, or any other suitable shape. Hooks 34 may be unidirectional, bi-directional, or omni-directional depending upon the application and companion loop fibers 32. Hooks 34 must be chosen in conjunction with companion loop fibers 32 so as to provide the peel and shear forces that are required for different applications.

Hook member 36 and loop fibers 32 ideally are chosen to provide shear strength greater than the elastic tension exerted by wrap 10 during use. Hook member 36, which has been found to work particularly well, comprises hooks 34 which are harpoon shaped and are oriented parallel to longitudinal axis 18 of material 12. Such hooks are available as 960E from Aplix, Charlotte, N.C. Hook member 36 is permanently attached to back wrap 10 by means of ultrasonic bonding, pressure bonding, adhesives, and/or stitching.

Landing zone 31 comprising loop fibers 32 may be any number of materials including, but not limited to, woven, knit, and nonwoven materials that have either been formed with loop fiber or have been subjected to post processing such as brushing or napping to expose more loop fibers. A preferred material is knit nylon landing zone material available as style #18904 from Guilford Fabrics, Greensboro, N.C.

Preferably, flexible material 12 has a first fibrous layer 60 at outer surface 30, a second fibrous layer 62 at body-facing side 28, and an elastic laminate 63 interposed therebetween. Elastic laminate 63 comprises an elastic member 64, a carrier layer 65 and a bulking layer 66. In a preferred embodiment elastic member 64 is thermally bonded to carrier layer 65 which in turn is attached to bulking layer 66 to form elastic laminate 63. In a more preferred embodiment, elastic member 64 is an elastic mesh which is integrally thermally bonded between a first carrier layer and a second carrier layer. Elastic laminate 63 extends from first end 14 to thermal pack 50.

Carrier layer 65 may be selected from any number of materials that are capable of withstanding thermal bonding temperature and sufficiently strong to carry elastic member 64. These materials include, but are not limited to, wovens, knits, carded nonwovens, spunbond nonwovens, and the like. These fabrics may be made of either natural or synthetic fibers including, but not limited to, polypropylene, polyester, nylon, rayon, cotton, cellulose, and the like. A material that has been successfully used is a 32 g/m$^2$ (27 grams per square yard (gsy)) thermally bonded carded polypropylene nonwoven available as grade #9327786 from Veratec, Walpole, Mass.

Elastic member 64 can be selected from natural or synthetic rubber, or any number of polymeric materials which are capable of elongation and recovery. Suitable materials include, but are not limited to, Styrene Block Copolymers, rubber, Lycra™, (a trademark of E. I. DuPont De Nemours, Wilmington, Del.), and Krayton™ (a trademark of Shell Oil Co., Houston, Tex.). They may also include polyethylenes including metallocene catalyst PE, foams including polyurethane and polyester, and the like. Elastic member 64 can be in the form of: strands, scrims, ribbons, tapes, structural elastic-like films. A material that has been used successfully is an elastic scrim available as T50018 from Conwed Plastics, Minneapolis, Minn.

Bulking layer 66 may be any number of different materials including, but not limited to, woven or knit fabrics, formed films, carded nonwovens, spunbond nonwovens, and the like. A material that has been found to be particularly suitable for bulking layer 66 is a polyethylene formed film available as C3265 from Tredeger Film Products, Terre Haute, Ind.

First fibrous layer 60 and second fibrous layer 62 may be any number of different materials including, but not limited to, wovens, knits, carded nonwovens, spunbond nonwovens, and the like. These fabrics may be made of either natural or synthetic fibers including, but not limited to, polypropylene, polyethylene, polyester, nylon, rayon, cotton, cellulose, and the like. A material that has been successfully used is a 32 g/m$^2$ (27 gsy) thermally bonded carded polypropylene nonwoven available as grade #9327786 from Veratec, Walpole, Mass.

Bonding of elastic member 64, carrier layer 65, and bulking layer 66 to form elastic laminate 63 may be done in any number of ways including, but not limited to, double sided adhesive tapes, hot melt adhesive, pressure sensitive adhesives, ultrasonic bonding, thermal bonding, pressure bonding, and mixtures thereof. Adhesives, if used, can be applied via hot melt beads, foam, spiral hot melt, melt blown, spray, immersion, transfer, or combinations thereof. Preferably, an adhesive layer 69 is used. Suitable elastic properties can be achieved via a number of construction techniques including, but not limited to, lamination with strained elastic, zero-strain elastics with subsequent activation in either machine direction or cross direction, or a combination of these techniques.

Elastic back wrap 10 preferably further comprises a first stiffening layer 52 and a second stiffing layer 53. Stiffening layers 52 and 53 are located adjacent second fibrous layer 62 extending from second end 16 to, and preferably overlapping, elastic laminate 63. Alternatively, a single stiffening layer may be used.

First stiffening layer 52 and second stiffening layer 53 may be chosen from any number of suitable materials which provide added rigidity in a direction transverse longitudinal axis 18. Suitable materials include, but are not limited to, wovens, knits, carded nonwovens, spunbond nonwovens, meltblown, combinations thereof, and the like. These fabrics may be made of either natural or synthetic fibers including, but not limited to, polypropylene, polyester, nylon, rayon, cotton, cellulose, combinations thereof, and the like. These materials may be post processed to increase their stiffness. This post processing may include calandering, embossing, bonding, and the like. A material which has been used successfully for first stiffening layer 52 is a spunbond/meltblown/spunbond (SMS) laminate available as Ultramesh Grade #L4990.4, form Veratec, Walpole, Mass. A material which has been used successfully for second stiffening layer 53 is a 42 g/m$^2$ (35 gsy) polypropylene spunbond available as grade #91061, from Veratec, Walpole, Mass.

Attachment of the various layers to make back wrap 10 may be achieved by any number of attachment means known in the art. These include, but are not limited to, hot melt adhesive including spiral sprays, meltblown, control coat, and the like, latex adhesives applied via spray, printing, gravure, and the like, thermal bonding, ultrasonic, pressure bonding, and the like. Preferably, an adhesive layer 69 is used. One particular method that has been used successfully for adhesive layer 69 is a hot melt adhesive available as 70-4589 from National Starch and Chemical Co., Bridgewater, N.J., applied via a spiral hot melt system at a rate of from about 32 to 65 mg/cm$^2$ (5 to 10 mg per square inch).

It is preferred, that back wrap 10 have a lightness measurement (L*) on outer surface 30 over heat cell(s) 22 of at least about 5 units greater than the lightness measurement on body-facing side 28 over heat cell(s) 22, to provide a contrast between the body side (inside of thermal back wrap 10) and clothing side (outside of thermal back wrap 10), making thermal back wrap 10 easier/more intuitive to the user to put on. An L* value of not less than about 65 and not greater than about 80 on the body-facing side 28, and about 78 or greater on outer surface 30 is preferred. These L* values are/may be achieved by adjusting, as appropriate, the number of layers and/or thickness (basis weight) of first fibrous layer 60 and/or bulking layer 66 and/or carrier layer 65 and/or second fibrous layer 62 and/or base layer 70 and/or cell covering layer 72.

Lightness may be measured using any suitable method and/or instrument for measuring lightness/chromaticity. One method which has been found useful uses a Minolta Chroma Meter CR-300, manufactured by Minolta Camera Company, Ramsey, N.J., wherein back wrap 10 is placed on a sheet of plain white paper and the measuring head placed on back wrap 10 at the specific site to be measured. L* values are recorded (an average of three measurements) at sites between heat cells 22 and sites directly over heat cells 22, on both the body-facing side 28 and outer surface 30. Methods, instrument information, and a definition of chromaticity may be found in the *Chroma Meter CR-300/CR-310/CR-321/CR-331/CR-331C Instruction Manual*, by The Minolta Camera Company, Ramsey, N.J., which is incorporated herein by reference in its entirety.

Elastic back wrap 10 further comprises one or more thermal packs 50. Each thermal pack 50, as indicated by dotted line 24, comprises a plurality of individual heat cells 22. Heat cells 22 are depicted in FIG. 1 extending into lower flap portion 54. Alternatively, lower flap portion 54 may be omitted and heat cells 22 repositioned on wrap 10 so as to be contained entirely between first edge 56 and second edge 58. Typically, the dimensions of pattern 24 are about 225 mm to about 400 mm measured in a direction parallel to longitudinal axis 18 and about 115 mm to about 200 mm measured in a direction transverse to longitudinal axis 18.

While thermal pack(s) 50 is most preferably positioned midway between first end 14 and second end 16 of flexible material 12, as indicated in FIGS. 1 and 2, thermal pack(s) 50 may alternatively be positioned anywhere along longitudinal axis 18 of flexible material 12 between first end 14 and second end 16, as appropriate.

Each thermal pack 50 comprises a plurality of individual heat cells 22, preferably embedded within the laminate structure of the thermal pack 50. Alternatively, each thermal pack 50 may comprise a single continuous base layer 70, wherein individual, or groups of heat cells 22 are fixedly attached and spaced apart across the base layer 70.

Heat cells 22 are spaced apart from each other and each heat cell 22 functions independently of the rest of the heat cells 22. While the heat cells may comprise any suitable composition providing heat, such as exothermic compositions, microwaveable compositions, heat of crystallization compositions, and the like, the preferred heat cell contains a densely packed, particulate exothermic composition 74 which substantially fills the available cell volume within the cell reducing any excess void volume thereby minimizing the ability of the particulate matter to shift within the cell. Alternatively, the exothermic composition 74 may be compressed into a hard tablet before being placed in each cell. Because the heat generating material is densely packed or compressed into a tablet, the heat cells 22 are not readily flexible. Therefore, the spacing apart of the cells and the materials selected for cell forming base layer 70 and cell covering layer 72 between the heat cells 22 allows each thermal pack 50 to easily conform to the user's body.

Cell forming base layer 70 and cell covering layer 72 are preferably continuous layers which may be made of any number of suitable materials. Preferably, cell forming base layer 70 and cell covering layer 72 comprise materials which are semirigid at a temperature of about 25° C. and which soften, i.e., become substantially less rigid, at a temperature of about 35° C., or greater. That is, the materials preferably have a tensile strength, within the elastic deformation range of the material, of about 0.7 g/mm² or greater, more preferably about 0.85 g/mm² or greater, most preferably about 1 g/mm² or greater, at about 25° C. and a tensile strength substantially less at about 35° C. or greater. "Substantially less", as used herein, means that the tensile strength of the material at about 35° C., or greater, is statistically significantly less than the tensile strength at about 25° C., at an appropriate statistical confidence (i. e., 95%) and power (i. e., >90%). Therefore, when heat cells 22, which are fixed within or to the unified structure of thermal pack 50, are active, that is at a heat cell temperature of from about 35° C. to about 60° C., preferably from about 35° C. to about 50° C., more preferably from about 35° C. to about 45° C., and most preferably from about 35° C. to about 40° C., the narrow portion of the continuous layer or layers of material immediately surrounding each heat cell softens and acts as a hinge between the heat cells and between any remaining, cooler, more rigid portions of the continuous layer or layers, bending preferentially more than either the heat cells or any more rigid portion. This results in thermal packs 50 which possess sufficient rigidity to maintain structural support of the heat cells and to prevent unacceptable stretching of structures of the continuous layer or layers during processing or use, while still maintaining good overall drape characteristics when heated.

When thermal packs 50 of the present invention are incorporated into back wrap 10, back wrap 10 easily adapts to a wide variety of body contours, provides consistent, convenient, and comfortable heat application, and an excellent conformity with body forms, while retaining sufficient rigidity to prevent wrap 10 from folding or bunching during use and deter easy access to heat cell contents.

Typically, the tensile strength is measured using a simple tensile test on an electronic tensile test apparatus, such as a universal constant rate elongation tensile testing machine with computer, Instron Engineering Corp., Canton, Mass. Any standard tensile test may be used, for example, material samples are cut into strips having a width of about 2.54 cm (about 1 inch) and a length of from about 7.5 cm to about 10 cm (about 3 to about 4 inches). The ends of the strips are placed into the jaws of the apparatus with enough tension to eliminate any slack, but without loading the load cell. The temperature of the sample is then allowed to stabilize at the desired test temperature. The load cell of the apparatus is set for about 22.7 kg (50 pound) load, the elongation set for 5 mm, and the crosshead speed is set for about 50 cm/min. The apparatus is started and the tensile strength data is collected by the computer. The sample is then removed from the apparatus.

The tensile strength may be calculated as the slope of the tensile load vs. the extension during elastic deformation of the materials using the equation:

$$m=(L/E)$$

Where m=the slope in g/mm² during elastic deformation;
L=the load at extension in g/mm; and
E=the extension in mm.

The continuous layers of cell forming base layer 70 and/or cell covering layer 72 also preferably comprise at least two-dimensional drape at about 25° C., i. e., a single fold line occurs in the material along a single axis, and preferably three-dimensional drape at about 35° C. or greater, i. e., two or more fold lines occur along multiple axes. Drape may be determined by placing and centering a square sample, for example about 30 cm by about 30 cm (about 12 inches by about 12 inches), of material on the end of a cylindrical shaft with a pointed end, allowing the material to drape due to gravitational forces, and the number of fold lines counted. Materials that exhibit one-dimensional drape, i. e., have no fold lines in any direction, are determined to be rigid, while materials that exhibit at least two-dimensional drape, i. e., have at least one fold line forming along at least one axis, are determined to be semirigid.

Different materials may be capable of satisfying the specified requirement for continuous cell forming base and/or cell covering layers 70 and/or 72, provided that the thickness is adjusted accordingly. Such materials may include, but are not limited to, polyethylene, polypropylene, nylon, polyester, polyvinyl chloride, polyvinylidene chloride, polyurethane, polystyrene, saponified ethylene-vinyl acetate copolymer, ethylene-vinyl acetate copolymer, natural rubber, reclaimed rubber, synthetic rubber, and mixtures thereof. These materials may be used alone, preferably extruded, more preferably coextruded, most preferably coextruded with a low melt temperature polymer including, but not limited to, ethylene vinyl acetate copolymer, low density polyethylene, and mixtures thereof.

Cell forming base layer 70 and/or cell covering layer 72 preferably comprise polypropylene, more preferably a coextruded material comprising polypropylene, most preferably a coextruded material wherein a first side comprises polypropylene, preferably from about 10% to about 90%, more preferably from about 40% to about 60%, of the total thickness of the material, and a second side comprises a tie-layer of a low melt temperature copolymer, preferably EVA. Cell forming base layer 70 and/or cell covering layer 72 preferably have a basis weight thickness of less than about 100 μm, more preferably less than or equal to about 75 μm, most preferably less than or equal to about 50 μm.

More preferably, base layer 70 and/or cover layer 72 comprise a coextruded material, having a first side of polypropylene and a second side of EVA.

Cell forming base layer 70 and/or preferably comprise a coextruded material, having a first side of polypropylene and a second side of EVA. Preferably cell covering layer 72 has a thickness of from about 20 μm to about 30 μm, preferably about 25 μm, and base layer 70 has a thickness of from about 20 μm to about 30 μm, preferably about 25 μm, more preferably cell covering layer 72 has a thickness of from about 40 μm to about 60 μm, more preferably about 50 μm (2 mils), and base layer 70 has a thickness of from about 20 μm to about 30 μm, preferably about 25 μm (1 mil), wherein the polypropylene comprises about 50% and the EVA tie-layer comprises about 50%, of the total thickness of cell forming base layer 70 or cell covering layer 72. A particularly suitable material is available as P18-3161 from Clopay Plastics Products, Cincinnati, Ohio. The P18-3161 which is preferred for cell covering layer 72 has been subjected to a post process aperturing with hot needles to render it permeable to oxygen.

When coextruded materials of the type just described are used for cell forming base layer 70 and cell covering layer 72, the EVA sides are preferably oriented toward each other to facilitate thermal bonding of cell covering layer 72 to cell forming base layer 70.

Good overall drape characteristics and/or excellent conformity with user's back, and/or increased structural support to the thermal pack 50, may also be achieved by selectively placing the heat cells 22 into positions fixed within or to the unified structure of the thermal pack 50 relative to each other which are sufficiently close so as to block some or all possible axes across the material of the continuous layer and/or layers 70 and/or 72, which otherwise would have passed uninterrupted between the heat cells 22, through the thermal pack 50, or select regions thereof, to minimize or eliminate undesirable, uninterrupted fold lines. That is, placement of the heat cells 22 into positions relative to each other which are sufficiently close so that the number of axes which pass uninterrupted, between the heat cells 22, is selectively controlled, such that the continuous cell forming base layer 70 and cell covering layer 72 of thermal pack 50, or select regions thereof, preferably folds along a multiplicity of short interconnected fold lines oriented in a number of different directions relative to each other. Folding along a multiplicity of interconnected fold lines results in thermal packs 50 which have good overall drape characteristics, readily conform with user's back, and/or have increased structural support of the heat cell matrix.

Because heat cells 22 are not readily flexible, the spacing between heat cells 22 provides the preferred benefits and may be determined, when selectively placing heat cells 22 within or fixed to the unified structure of thermal packs 50, wherein at least one heat cell of four adjacent heat cells, whose centers form a quadrilateral pattern, blocks one or more axes that could otherwise form at least one fold line tangential to the edges of one or more pairings of the remaining three heat cells in the quadrilateral pattern. Preferably, the spacing between at least one heat cell of the four adjacent heat cells and each of the heat cells of the one or more pairings of the remaining heat cells in the quadrilateral pattern may be calculated using the equation:

$$s \leq (W_q/2)*0.75$$

Where s=the closest distance between the heat cells; and $W_q$=the measurement of the smallest diameter of the smallest diameter heat cell within the quadrilateral pattern.

Alternatively, the spacing between heat cells 22 may be determined wherein, at least one heat cell of three adjacent heat cells, whose centers form a triangular pattern, blocks one or more axes that could otherwise form at least one fold line tangential to the edges of the remaining pair of heat cells in the triangular pattern formed by the three heat cells. Most preferably, the spacing between the at least one heat cell of the three adjacent heat cells and each heat cell of the remaining pair of heat cells in the triangular pattern may be calculated using the equation:

$$s < (W_t/2)*0.3$$

Where s=the closest distance between the heat cells; and $W_t$=the measurement of the smallest diameter of the smallest diameter heat cell within the triangular pattern.

Different materials may be capable of satisfying the above specified requirements. Such materials may include, but are not limited to, those materials mentioned above.

A most preferred embodiment of the disposable thermal packs 50 of the present invention comprises at least one continuous layer of semirigid material having the thermophysical properties described above, and the heat cells 22 fixed within or to the unified structure of thermal pack 50 in positions relative to each other which are sufficiently close so as to block some or all possible axes across the material of the continuous layer(s) 70 and/or 72, which otherwise would have passed uninterrupted between heat cells 22, through thermal packs 50, or select regions thereof, to minimize or eliminate undesirable, uninterrupted fold lines, as described above.

Exothermic composition 74 may comprise any composition capable of providing heat. However, exothermic composition 74 preferably comprises a particulate mix of chemical compounds that undergo an oxidation reaction during use. Alternatively, exothermic composition 74 may also be formed into agglomerated granules, direct compacted into compaction articles such as granules, pellets, tablets, and/or slugs, and mixtures thereof. The mix of compounds typically comprises iron powder, carbon, a metal salt(s), and water. Mixtures of this type, which react when exposed to oxygen, provide heat for several hours.

Suitable sources for iron powder include cast iron powder, reduced iron powder, electrolytic iron powder, scrap iron powder, pig iron, wrought iron, various steels, iron alloys, and the like and treated varieties of these iron powders. There is no particular limitation to their purity, kind, etc. so long as it can be used to produce heat-generation with electrically conducting water and air. Typically, the iron powder comprises from about 30% to about 80% by weight, preferably from about 50% to about 70% by weight, of the particulate exothermic composition.

Active carbon prepared from coconut shell, wood, charcoal, coal, bone coal, etc. are useful, but those prepared from other raw materials such as animal products, natural gas, fats, oils and resins are also useful in the particulate exothermic composition of the present invention. There is no limitation to the kinds of active carbon used, however, the preferred active carbon has superior water holding capabilities and the different carbons may be blended to reduce cost. Therefore, mixtures of the above carbons are useful in the present invention as well. Typically, activated carbon, non-activated carbon, and mixtures thereof, comprises from about 3% to about 25%, preferably from about 8% to about 20%, most preferably from about 9% to about 15% by weight, of the particulate exothermic composition.

The metal salts useful in the particulate exothermic composition include sulfates such as ferric sulfate, potassium sulfate, sodium sulfate, manganese sulfate, magnesium sulfate; and chlorides such as cupric chloride, potassium chloride, sodium chloride, calcium chloride, manganese chloride, magnesium chloride and cuprous chloride. Also, carbonate salts, acetate salts, nitrates, nitrites and other salts can be used. In general, several suitable alkali, alkaline earth, and transition metal salts exist which can also be used, alone or in combination, to sustain the corrosive reaction of iron. The preferred metal salts are sodium chloride, cupric chloride, and mixtures thereof. Typically, the metal salt(s) comprises from about 0.5% to about 10% by weight, preferably from about 1.0% to about 5% by weight, of the particulate exothermic composition.

The water used in the particulate exothermic composition may be from any appropriate source. There is no particular limitation to its purity, kind, etc. Typically, water comprises from about 1% to about 40% by weight, preferably from about 10% to about 30% by weight, of the particulate exothermic composition.

Additional water-holding materials may also be added as appropriate. Useful additional water-holding materials include vermiculite, porous silicates, wood powder, wood flour, cotton cloth having a large amount of fluffs, short fibers of cotton, paper scrap, vegetable matter, super absorbent water-swellable or watersoluble polymers and resins, carboxymethylcellulose salts, and other porous materials having a large capillary function and hydrophilic property can be used. Typically, the additional water-holding materials comprise from about 0.1% to about 30% by weight, preferably from about 5% to about 20% by weight, most preferably from about 1% to about 10% by weight, of the particulate exothermic composition.

Other additional components include agglomeration aids such as gelatin, natural gums, cellulose derivatives, cellulose ethers and their derivatives, starch, modified starches, polyvinyl alcohols, polyvinylpyrrolidone, sodium alginates, polyols, glycols, corn syrup, sucrose syrup, sorbitol syrup and other polysaccharides and their derivatives, polyacrylamides, polyvinyloxoazolidone, and maltitol syrup; dry binders such as maltodextrin, sprayed lactose, co-crystallized sucrose and dextrin, modified dextrose, sorbitol, mannitol, microcrystalline cellulose, microfine cellulose, pre-gelatinized starch, dicalcium phosphate, and calcium carbonate; oxidation reaction enhancers such as elemental chromium, manganese, or copper, compounds comprising said elements, or mixtures thereof; hydrogen gas inhibitors such as inorganic or organic alkali compounds or alkali weak acid salts including sodium hydroxide, potassium hydroxide, sodium hydrogen carbonate, sodium carbonate, calcium hydroxide, calcium carbonate, and sodium propionate; fillers such as natural cellulosic fragments including wood dust, cotton linter, and cellulose, synthetic fibers in fragmentary form including polyester fibers, foamed synthetic resins such as foamed polystyrene and polyurethane, and inorganic compounds including silica powder, porous silica gel, sodium sulfate, barium sulfate, iron oxides, and alumina; and anti-caking agents such as tricalcium phosphate and sodium silicoaluminate. Such components also include thickeners such as cornstarch, potato starch, carboxymethylcellulose, and a-starch, and surfactants such as those included within the anionic, cationic, nonionic, zwitterionic, and amphoteric types. The preferred surfactant, if used however, is nonionic. Still other additional components which may be added to the particulate exothermic compositions of the present invention, as appropriate, include extending agents such as metasilicates, zirconium, and ceramics.

Preferably at least 50%, more preferably 70%, even more preferably 80% and most preferably 90% of all of the particles by weight of the particulate exothermic composition of the present invention have a mean particle size of less than 200 $\mu$m, preferably less than 150 $\mu$m.

The above-mentioned components of the composition are blended using conventional blending techniques. Suitable methods of blending these components are described in detail in U. S. Pat. No. 4,649,895 to Yasuki et al., issued Mar. 17, 1987 which is incorporated by reference herein in its entirety.

Alternatively to the above described particulate exothermic composition, the exothermic composition may be formed into agglomerated granules, direct compacted into compaction articles such as granules, pellets, tablets, and/or slugs, and mixtures thereof.

The exothermic composition of these agglomerated granules and/or compaction articles comprises iron powder, dry powdered carbonaceous material, an agglomeration aid, and a dry binder. Additionally, a metal salt, is added to the dry mix or subsequently as an aqueous/brine solution. Typically, the iron powder comprises from about 30% to about 80%, preferably from about 40% to about 70%, most preferably from about 50% to about 65% by weight; activated carbon, non-activated carbon, and mixtures thereof, comprises from about 3% to about 20%, preferably from about 5% to about 15%, most preferably from about 6% to about 12% by weight; the metal salt(s) comprises from about 0.5% to about 10%, preferably from about 1% to about 8%, most preferably from about 2% to about 6% by weight; the agglomeration aids comprise from about 0% to about 9%, preferably from about 0.5% to about 8%, more preferably from about 0.6% to about 6%, most preferably from about 0.7% to about 3% by weight; and the dry binder comprises from about 0% to about 35%, preferably from about 4% to about 30%, more preferably from about 7% to about 20%, most preferably from about 9% to about 15% by weight, of the agglomerated pre-compaction compositions of the present invention.

Heat cells comprising agglomerated granules are typically made using conventional blending techniques and agglomerated into granules.

Heat cells comprising compaction articles are preferably made by direct compaction of the dry ingredients into articles such as hard granules, pellets, tablets, and/or slugs. Suitable methods of making tablets and/or slugs are described in detail in Chapter 89, "Oral Solid Dosage Forms", *Remington's Pharmaceutical Sciences*, 18$^{th}$ Edition, (1990), pp. 1634–1656, Alfonso R. Gennaro, ed., incorporated herein by reference in its entirety. Any conventional tableting machine and compression pressures, up to the maximum provided by the machine can be used.

The tablets/slugs can have any geometric shape consistent with the shape of the heat cell, e.g., disk, triangle, square, cube, rectangle, cylinder, ellipsoid and the like, all or none of which may contain a hole through the middle or other reservoir. The preferred shape of the tablet/slug comprises a disk shaped geometry, having a concaved (whisper) configuration to the top and/or bottom of the tablet. The more preferred shape of the tablet/slug, however, comprises a disk shaped geometry, having a hole perpendicular to, and through the middle of the top and bottom of the tablet.

The size of the compacted disk is limited only by the size of the punches and die available and/or used in the tableting machine, as well as the size of the heat cell pocket. However, the disk typically has a diameter of from about 0.2 cm to about 10 cm, preferably from about 0.5 cm to about 8 cm, more preferably from about 1 cm to about 5 cm, and most preferably from about 1.5 cm to about 3 cm and a height of from about 0.08 cm to about 1 cm, preferably from about 0.15 cm to about 0.86 cm, more preferably from about 0.2 cm to about 0.6 cm, and most preferably from about 0.2 cm to about 0.5 cm. Alternatively, the compacted disk having a geometric shape other than a disk shape may have a width at its widest point of from about 0.15 cm to about 20 cm, preferably from about 0.3 cm to about 10 cm, more preferably from about 0.5 cm to about 5 cm, most preferably from about 1 cm to about 3 cm, a height at its highest point of from about 0.08 cm to about 1 cm, preferably from about 0.15 cm to about 0.8 cm, more preferably from about 0.2 cm to about 0.6 cm, and most preferably from about 0.2 cm to about 0.5 cm, and a length at its longest point of from about 1.5 cm to about 20 cm, preferably from about 1 cm to about 15 cm, more preferably from about 1 cm to about 10 cm, most preferably from about 3 cm to about 5 cm. The hole or reservoir should be large enough to substantially hold the prescribed amount of water and/or the water-carrying material. Typically, the hole has a diameter of from about 0.1 cm to about 1 cm, preferably from about 0.2 cm to about 0.8 cm, and more preferably from about 0.2 cm to about 0.5 cm.

The compaction articles of the present invention are compressed to the hardest possible mechanical strength to withstand the shocks of handling in their manufacture, packing, shipping, and dispensing. The compaction articles are typically compressed to a density of greater than about 1 g/cm$^3$, preferably from about 1 g/cm$^3$ to about 3 g/cm$^3$, more preferably from about 1.5 g/cm$^3$ to about 3 g/cm$^3$, and most preferably from about 2 g/cm$^3$ to about 3 g/cm$^3$.

Heat cells 22 comprising the above described components are typically formed by adding a fixed amount of a particulate exothermic composition or compaction article(s) 74 to a pocket or pockets made in a first continuous layer, i. e., cell base layer 70. A second continuous layer, i. e., cell covering layer 72, is placed over the first continuous layer, sandwiching the particulate exothermic composition or compaction article(s) between the two continuous layers which are then bonded together, preferably using a low heat, forming a unified, laminate structure. Preferably, each heat cell has a similar volume of heat generating material and has similar oxygen permeability means. However, the volume of the heat generating material, shape of the heat cell, and oxygen permeability may be different from heat cell to heat cell as long as the resulting cell temperatures generated are within accepted therapeutic and safety ranges for their intended use.

The heat cells 22 of thermal pack 50 can have any geometric shape, e.g., disk, triangle, pyramid, cone, sphere, square, cube, rectangle, rectangular parallelepiped, cylinder, ellipsoid and the like. The preferred shape of the heat cells 22 comprises an ellipsoid (i. e., oval), having a width at its widest point of from about 0.15 cm to about 20 cm, preferably from about 0.3 cm to about 10 cm, more preferably from about 0.5 cm to about 5 cm, most preferably from about 1 cm to about 3 cm, a height at its highest point of from greater than about 0.2 cm to about 5 cm, preferably from greater than about 0.2 cm to about 1 cm, more preferably from greater than about 0.2 cm to about 0.8 cm, and most preferably from about 0.3 cm to about 0.7 and a length at its longest point of from about 0.5 cm to about 20 cm, preferably from about 1 cm to about 15 cm, more preferably from about 1 cm to about 10 cm, most preferably from about 3 cm to about 5 cm. Alternatively, the heat cells may comprise a disk shape, preferably having a cell diameter of from about 0.2 cm to about 10 cm, preferably from about 0.5 cm to about 8 cm, more preferably from about 1 cm to about 5 cm, and most preferably from about 1.5 cm to about 3 cm. The heat cells 75 have a height of from greater than about 0.2 cm to about 1 cm, preferably from greater than about 0.2 cm to about 0.9 cm, more preferably from greater than about 0.2 cm to about 0.8 cm, and most preferably from greater than about 0.3 cm to about 0.7 cm The ratio of fill volume to cell volume of the heat cells 22 is from about 0.7 to about 1.0, preferably from about 0.75 to about 1.0, more preferably from about 0.8 to about 1.0, even more preferably from about 0.85 to about 1.0, and most preferably from about 0.9 to about 1.0.

Oxygen permeability in cell covering layer 72 is preferably a plurality of apertures in cell covering layer 72, which are made by piercing cell covering layer 72 with hot needles. The size of the apertures is preferably about 0.127 mm diameter, and there are preferably 25 to 40 apertures per heat cell 22. Another preferred method of making apertures is to pierce cell covering layer 72 with cold needles. Alternatively, apertures may be produced by a vacuum forming or a high pressure water jet forming process. Yet another method is making cell covering layer 72 from a microporous membrane or a semi-permeable membrane. Such membrane may be combined with a highly porous carrier material to facilitate processing. The oxygen permeability required ranges from about 0.01 cc $O_2$ per minute per 5 square cm to about 15 cc $O_2$ per minute per 5 square cm at 21° C. and 1 ATM.

The velocity, duration, and temperature of the thermogenic oxidation reaction of the exothermic composition 74 can be controlled as desired by changing the area of contact with air, more specifically, by changing the oxygen diffusion/permeability.

Using the materials described above for construction of wrap 10, most people typically can be accommodated with only two different sizes of wrap 10. For example the smaller size of wrap 10 has a dimension of from about 850 mm to about 950 mm measured in a direction parallel to the longitudinal axis 18 when wrap 10 is in a relaxed or untensioned state and a dimension of about 125 mm to about 150 mm measured in a direction transverse to the longitudinal axis 18. The larger size of wrap 10 has a dimension of from about 1100 mm to about 1400 mm measured in a direction parallel to the longitudinal axis 18 when wrap 10 is in a relaxed or untensioned state and a dimension of about 135 mm to about 150 mm measured in a direction transverse to the longitudinal axis 18.

The disposable thermal back wraps of the present invention may optionally incorporate a component, such as a separate substrate layer or incorporated into at least one of the continuous layers, comprising active aromatic compounds, non-active aromatic compounds, pharmaceutical actives or other therapeutic agents, and mixtures thereof, to be delivered through the skin. Such active aromatic compounds include, but are not limited to, menthol, camphor, and eucalyptus. Such non-active aromatic compounds include, but are not limited to, benzaldehyde, citral, decanal, and aldehyde. Such pharmaceutical actives/therapeutic agents include, but are not limited to antibiotics, vitamins, antiviral agents, analgesics, anti-inflammatory agents, antipruritics, antipyretics, anesthetic agents, antifingals, antimicrobials, and mixtures thereof. The disposable thermal back wraps may also comprise a separate substrate layer, or incorporated into at least one of the continuous layers, a self-adhesive component and/or a sweat-absorbing component.

The finished disposable thermal back wraps are typically packaged in a secondary package. An air-impermeable package may be used to prevent an oxidation reaction from occurring until desired as described in U.S. Pat. No. 4,649,895, incorporated herein by reference in its entirety. Alternatively, other means may also be used to prevent an oxidation reaction from occurring before desired, such as air impermeable removable adhesive strips placed over the aeration holes in the heat cells such that, when the strips are removed, air is allowed to enter the heat cells, thus activating the oxidation reaction of the iron powder.

The present invention further comprises a method for treating acute, recurrent, and/or chronic back pain, including muscular, skeletal, and/or referred back pain, of a person suffering such pain by topically applying heat to the specific areas of the back of a person suffering such pain. The method comprises maintaining a skin temperature to the specific areas of the back of a person suffering such pain of from about 32° C. to about 50° C., preferably from about 32° C. to about 45° C., more preferably from about 32° C. to about 42° C., most preferably from about 32° C. to about 39° C., still most preferably from about 32° C. to about 37° C., preferably by applying the above described back wraps to the back of a person suffering such pain, for from about twenty seconds to about twenty-four hours, preferably from about twenty minutes to about twenty hours, more preferably from about four hours to about sixteen hours, most preferably from about eight hours to about twelve hours, wherein the maximum skin temperature and the length of time of maintaining the skin temperature at the maximum skin temperature may be appropriately selected by a person needing such treatment, such that the desired therapeutic benefits are achieved, without any adverse events, such as skin burns which may be incurred by using a high temperature for a long period of time.

Preferably the method comprises maintaining a sustained skin temperature to the back of a person having acute, recurrent, and/or chronic back pain, including muscular, skeletal, and/or referred back pain, of from about 32° C. to about 43° C., preferably from about 32° C. to about 42° C., more preferably from about 32° C. to about 41° C., most preferably from about 32° C. to about 39° C., still most preferably from about 32° C. to about 37° C., for a time period of greater than about 1 hour, preferably greater than about 4 hours, more preferably greater than about 8 hours, even more preferably greater than about 16 hours, most preferably about 24 hours, to substantially relieve acute, recurrent, and/or chronic back pain, including skeletal, muscular, and/or referred back pain, of a person having such pain and to substantially prolong relief, for at least about 2 hours, preferably for at least about 8 hours, more preferably for at least about 16 hours, most preferably for at least about one day, still most preferably for at least about three days, from such pain, even after the heat source is removed from the back of the user.

While particular embodiments of the present invention have been illustrated and described, it will be obvious to those skilled in the art that various changes and modifications may be made without departing from the spirit and scope of the invention, and it is intended to cover in the appended claims all such modifications that are within the scope of the invention.

What is claimed is:

1. A disposable thermal back wrap comprising:
   a) at least one substantially rectangular piece of flexible material having a first end, a second end, and one or more elastic portions therebetween said first end and said second end wherein said elastic portion is stretchable along a longitudinal axis of said piece of flexible material;
   b) one or more thermal packs, said thermal pack having a unified structure comprising at least one continuous layer of a semirigid material having a tensile strength of about 0.7 $g/mm^2$, or greater, and at least two-dimensional drape at a temperature of about 25° C., and wherein said material has a tensile strength, at a temperature of about 35° C. or greater, substantially less than said tensile strength of said material at about 25° C., and having a plurality of individual heat cells spaced apart and fixed within or to said unified structure of said thermal pack; and
   c) a fastening means in order to hold said thermal back wrap around said user's torso.

2. A disposable thermal back wrap according to claim 1 wherein said at least one continuous layer comprises a tensile strength of about 0.85 $g/mm^2$, or greater, and at least two-dimensional drape at a temperature of about 25° C.

3. A disposable thermal back wrap according to claim 2 wherein said at least one continuous layer comprises a tensile strength of about 1 $g/mm^2$, or greater, and at least two-dimensional drape at a temperature of about 25° C.

4. A disposable thermal back wrap according to claim 1 wherein said at least one continuous layer comprises a material selected from the group consisting of polyethylene, polypropylene, nylon, polyester, polyvinyl chloride, polyvinylidene chloride, polyurethane, polystyrene, saponified ethylene-vinyl acetate copolymer, ethylene-vinyl acetate copolymer, natural rubber, reclaimed rubber, synthetic rubber, and mixtures thereof.

5. A disposable thermal back wrap according to claim 4 wherein said at least one continuous layer comprises an extruded material selected from the group consisting of polyethylene, polypropylene, nylon, polyester, polyvinyl chloride, polyvinylidene chloride, polyurethane, polystyrene, saponified ethylene-vinyl acetate copolymer, ethylene-vinyl acetate copolymer.

6. A disposable thermal back wrap according to claim 5 wherein said at least one continuous layer comprises a coextruded material having a first side selected from the group consisting of polyethylene, polypropylene, nylon, polyester, polyvinyl chloride, polyvinylidene chloride, polyurethane, and polystyrene, and a second side selected from the group consisting of saponified ethylene-vinyl acetate copolymer and ethylene-vinyl acetate copolymer.

7. A disposable thermal back wrap according to claim 6 wherein said at least one continuous layer comprises a coextruded material having a first side of polypropylene and a second side of ethylene-vinyl acetate copolymer.

8. A disposable thermal back wrap according to claim 7 wherein said at least one continuous layer comprises a coextruded material having a first side of polypropylene and a second side of ethylene vinyl acetate copolymer, wherein said polypropylene comprises from about 10% to about 90% of the total thickness of said material.

9. A disposable thermal back wrap according to claim 8 wherein said at least one continuous layer comprises a coextruded material having a first side of polypropylene and a second side of ethylene vinyl acetate copolymer, wherein said polypropylene comprises from about 40% to about 60% of the total thickness of said material.

10. A disposable thermal back wrap according to claim 1 wherein said fastening means is reclosable.

11. A disposable thermal back wrap according to claim 10 wherein said reclosable fastening means comprises a hook and loop fastening system.

12. A disposable thermal back wrap according to claim 11 wherein said hook and loop fastening system comprises a two-part hook and loop fastening system.

13. A disposable thermal back wrap according to claim 1 wherein said disposable elastic thermal back wrap further comprises a lower flap portion extending outwardly from second edge.

14. A disposable thermal back wrap according to claim 1 wherein said disposable elastic thermal back wrap further comprises one or more stiffening layers.

15. A disposable thermal back wrap according to claim 1 wherein said heat cells comprise a shape selected from the group consisting of a disk, triangle, pyramid, cone, sphere, square, cube, rectangle, rectangular parallelepiped, cylinder, and ellipsoid, said disk having a diameter of from about 1 cm to about 5 cm and a height of from greater than about 0.2 cm to about 1 cm, and said triangle, pyramid, cone, sphere, square, cube, rectangle, rectangular parallelepiped, cylinder, and ellipsoid having a width at its widest point of from about 0.5 cm to about 5 cm and a height at its highest point of from greater than about 0.2 cm to about 1 cm and a length at its longest point of from about 1.5 cm to about 10 cm, and wherein further said heat cells, when filled with an exothermic composition, have a fill volume to cell volume ratio of from about 0.7 to about 1.0.

16. A disposable thermal back wrap according to claim 15 wherein said exothermic composition comprises:
a.) from about 30% to about 80% by weight, iron powder;
b.) from about 3% to about 25% by weight, carbonaceous material selected from the group consisting of activated carbon, non-activated carbon, and mixtures thereof;
c.) from about 0.5% to about 10% by weight, metal salt; and
d.) from about 1% to about 40% by weight, water.

17. A disposable thermal back wrap according to claim 16 wherein said exothermic composition further comprises from about 0.1% to about 30% by weight, of additional water-holding material.

18. A disposable thermal back wrap according to claim 15 wherein said exothermic composition comprises:
a.) from about 30% to about 80% by weight, of iron powder;
b.) from about 3% to about 20% by weight, carbonaceous material selected from the group consisting of activated carbon, non-activated carbon, and mixtures thereof;
c.) from about 0% to about 9% by weight, of an agglomeration aid selected from the group consisting of corn syrup, maltitol syrup, crystallizing sorbitol syrup, amorphous sorbitol syrup, and mixtures thereof; and
d.) from about 0% to about 35% by weight, of a dry binder selected from the group consisting of microcrystalline cellulose, maltodextrin, sprayed lactose, co-crystallized sucrose and dextrin, modified dextrose, mannitol, microfine cellulose, pre-gelatinized starch, dicalcium phosphate, calcium carbonate, and mixtures thereof;
wherein from about 0.5% to about 10% by weight, of a metal salt selected from the group consisting of alkali metal salts, alkaline earth metal salts, transitional metal salts, and mixtures thereof is added to said composition as part of the dry mix or subsequently in an aqueous solution as brine, and wherein said exothermic composition comprises a physical form selected from the group consisting of dry agglomerated granules, direct compaction articles, and mixtures thereof, wherein said direct compaction articles are selected from the group consisting of granules, pellets, tablets, slugs, and mixtures thereof, and wherein said tablets and slugs comprise a geometric shape selected from the group consisting of disk, triangle, square, cube, rectangle, cylinder, and ellipsoid, said disk having a diameter of from about 1 cm to about 5 cm and a height of from about 0.08 cm to about 1 cm and said triangle, square, cube, rectangle, cylinder, and ellipsoid having a width at its widest point of from about 0.5 cm to about 5 cm and a height at its highest point of from about 0.08 cm to about 1 cm and a length at its longest point of from about 1 cm to about 10 cm.

19. A disposable thermal back wrap according to claim 18 wherein said exothermic composition further comprises from about 0.5% to about 10% by weight, of additional water-holding materials selected from the group consisting of acrylic acid salt starch co-polymer, isobutylene maleic anhydride co-polymer, vermiculite, carboxymethylcellulose, and mixtures thereof.

20. A disposable thermal back wrap according to claim 18 wherein said dry binder comprises from about 4% to about 30% by weight, of microcrystalline cellulose.

21. A disposable thermal back wrap according to claim 18 wherein said tablets comprise a geometric shape selected from the group consisting of a disk shape having a hole passing perpendicular to and through the middle of the top and bottom surfaces and a disk shape wherein the top and bottom surfaces are concaved forming a reservoir conducive to holding a liquid.

22. A disposable thermal back wrap according to claim 18 wherein said direct compaction articles comprise a density of greater than about 1 $g/cm^3$.

23. A disposable thermal back wrap according to claim 1 further comprising additional components selected from the group consisting of active aromatic compounds, non-active aromatic compounds, pharmaceutical actives, and mixtures thereof.

24. A disposable thermal back wrap comprising at least one thermal pack having a unified structure comprising at least one continuous layer of material and a plurality of individual heat cells placed into positions fixed within or to said unified structure of said thermal pack which are sufficiently close and relative to each other, so as to block some or all possible axes across said at least one continuous layer, which otherwise would have passed uninterrupted between said heat cells, through said thermal pack, or select regions thereof.

25. A disposable thermal back wrap according to claim 24 wherein at least one of said heat cells of four adjacent said heat cells, whose centers form a quadrilateral pattern, blocks one or more of said axes that could otherwise form at least one fold line tangential to the edges of one or more pairings of the remaining said heat cells in the quadrilateral pattern.

26. A disposable thermal back wrap according to claim 25 wherein the spacing between said at least one of said heat cells and each of said heat cells of said one or more pairings of said remaining heat cells in said quadrilateral pattern is the same or less than the spacing obtained by dividing the measurement of the smallest diameter of the smallest diameter heat cell of said heat cells within said quadrilateral pattern by 2 and multiplying the result by 0.75.

27. A disposable thermal back wrap according to claim 24 wherein at least one of said heat cells of three adjacent said heat cells, whose centers form a triangular pattern, blocks one or more of said axes that could otherwise form at least one fold line tangential to the edges of the remaining pair of said heat cells in the triangular pattern formed by said three heat cells.

28. A disposable thermal back wrap according to claim 27 wherein the spacing between said at least one of said heat cells and each of said heat cells of said remaining pair of said heat cells in said triangular pattern is the same or less than the spacing obtained by dividing the measurement of the smallest diameter of the smallest diameter heat cell of said heat cells within said triangular pattern by 2 and multiplying the result by 0.3.

29. A disposable thermal back wrap according to claim 24 wherein said at least one continuous layer comprises a semirigid material having a tensile strength of about 0.7 g/mm$^2$, or greater, and at least two-dimensional drape at a temperature of about 25° C., and wherein said material has a tensile strength, at a temperature of about 35° C. or greater, substantially less than said tensile strength of said material at about 25° C.

30. A disposable thermal back wrap according to claim 29 wherein said continuous layer comprises a material selected from the group consisting of polyethylene, polypropylene, nylon, polyester, polyvinyl chloride, polyvinylidene chloride, polyurethane, polystyrene, saponified ethylene-vinyl acetate copolymer, ethylene-vinyl acetate copolymer, natural rubber, reclaimed rubber, synthetic rubber, and mixtures thereof.

31. A disposable thermal back wrap according to claim 30 wherein said continuous layer comprises a coextruded material having a first side selected from the group consisting of polyethylene, polypropylene, nylon, polyester, polyvinyl chloride, polyvinylidene chloride, polyurethane, and polystyrene, and a second side selected from the group consisting of saponified ethylene-vinyl acetate copolymer and ethylene-vinyl acetate copolymer.

32. A disposable thermal back wrap according to claim 31 wherein said continuous layer comprises a coextruded material having a first side of polypropylene and a second side of ethylene-vinyl acetate copolymer.

33. A disposable thermal back wrap according to claim 24 wherein said heat cells comprise a shape selected from the group consisting of a disk, triangle, pyramid, cone, sphere, square, cube, rectangle, rectangular parallelepiped, cylinder, and ellipsoid, said disk having a diameter of from about 1 cm to about 5 cm and a height of from greater than about 0.2 cm to about 1 cm, and said triangle, pyramid, cone, sphere, square, cube, rectangle, rectangular parallelepiped, cylinder, and ellipsoid having a width at its widest point of from about 0.5 cm to about 5 cm and a height at its highest point of from greater than about 0.2 cm to about 1 cm and a length at its longest point of from about 1.5 cm to about 10 cm, and wherein said heat cells, when filled with an exothermic composition, have a fill volume to cell volume ratio of from about 0.7 to about 1.0.

34. A disposable thermal back wrap according to claim 33 wherein said exothermic composition comprises:

a.) from about 30% to about 80% by weight, iron powder;
b.) from about 3% to about 25% by weight, carbonaceous material selected from the group consisting of activated carbon, non-activated carbon, and mixtures thereof;
c.) from about 0.5% to about 10% by weight, metal salt; and
d.) from about 1% to about 40% by weight, water.

35. A disposable thermal back wrap according to claim 34 wherein said exothermic composition further comprises from about 0.1% to about 30% by weight, of additional water-holding material.

36. A disposable thermal back wrap according to claim 33 wherein said exothermic composition comprises:

a.) from about 30% to about 80% by weight, of iron powder;
b.) from about 3% to about 20% by weight, of carbonaceous material selected from the group consisting of activated carbon, non-activated carbon, and mixtures thereof;
c.) from about 0% to about 9% by weight, of an agglomeration aid selected from the group consisting of corn syrup, maltitol syrup, crystallizing sorbitol syrup, amorphous sorbitol syrup, and mixtures thereof; and
d.) from about 0% to about 35% by weight, of a dry binder selected from the group consisting of microcrystalline cellulose, maltodextrin, sprayed lactose, co-crystallized sucrose and dextrin, modified dextrose, mannitol, microfine cellulose, pre-gelatinized starch, dicalcium phosphate, calcium carbonate, and mixtures thereof;

wherein from about 0.5% to about 10% by weight, of a metal salt selected from the group consisting of alkali metal salts, alkaline earth metal salts, transitional metal salts, and mixtures thereof is added to said composition as part of the dry mix or subsequently in an aqueous solution as brine, and wherein further said exothermic composition comprises a physical form selected from the group consisting of dry agglomerated granules, direct compaction articles, and mixtures thereof, wherein said direct compaction articles are selected from the group consisting of granules, pellets, tablets, slugs, and mixtures thereof, and wherein said tablets and slugs comprise a geometric shape selected from the group consisting of disk, triangle, square, cube, rectangle, cylinder, and ellipsoid, said disk having a diameter of from about 1 cm to about 5 cm and a height of from about 0.08 cm to about 1 cm and said triangle, square, cube, rectangle, cylinder, and ellipsoid having a width at its widest point of from about 0.5 cm to about 5 cm and a height at its highest point of from about 0.08 cm to about 1 cm and a length at its longest point of from about 1 cm to about 10 cm.

37. A disposable thermal back wrap according to claim 36 wherein said exothermic composition further comprises from about 0.5% to about 10% by weight, of additional water-holding materials selected from the group consisting of acrylic acid salt starch co-polymer, isobutylene maleic anhydride co-polymer, vermiculite, carboxymethylcellulose, and mixtures thereof.

38. A disposable thermal back wrap according to claim 36 wherein said dry binder comprises from about 4% to about 30% by weight, of microcrystalline cellulose.

39. A disposable thermal back wrap according to claim 36 wherein said tablets comprise a geometric shape selected from the group consisting of a disk shape having a hole passing perpendicular to and through the middle of the top and bottom surfaces and a disk shape wherein said top and bottom surfaces are concaved forming a reservoir conducive to holding a liquid.

40. A disposable thermal back wrap according to claim 36 wherein said direct compaction articles comprise a density of greater than about 1 g/cm$^3$.

41. A disposable thermal back wrap according to claim 24 wherein said fastening means is reclosable.

42. A disposable thermal back wrap according to claim 41 wherein said reclosable fastening means comprises a hook and loop fastening system.

43. A disposable thermal back wrap according to claim 42 wherein said hook and loop fastening system comprises a two-part hook and loop fastening system.

44. A disposable thermal back wrap according to claim 24 wherein said disposable elastic thermal back wrap further comprises a lower flap portion extending outwardly from second edge.

45. A disposable thermal back wrap according to claim 24 wherein said disposable elastic thermal back wrap further comprises one or more stiffening layers.

46. A disposable thermal back wrap according to claim 24 further comprising additional components selected from the group consisting of active aromatic compounds, non-active aromatic compounds, pharmaceutical actives, and mixtures thereof.

47. A method of treating back pain, selected from the group consisting of acute muscular, acute skeletal, acute referred, recurrent muscular, recurrent skeletal, recurrent referred, chronic muscular, chronic skeletal, and chronic referred back pain, by applying a disposable thermal back wrap of claim 1 to the back of a person needing such treatment, to maintain a skin temperature to the back of from about 32° C. to about 50° C. for a time period of from about twenty seconds to about twenty-four hours, wherein said skin temperature and said period of time of maintaining said skin temperature is appropriately selected by said person needing such treatment, to substantially relieve said pain without adverse events.

48. A method of treating back pain according to claim 47 wherein said skin temperature is maintained from about 32° C. to about 39° C.

49. A method of treating back pain according to claim 47 wherein said skin temperature is maintained at a temperature of from about 32° C. to about 43° C. for a time period of greater than about 1 hour, wherein said relief of said pain is substantially prolonged for at least about 2 hours after removal of said heat from the back of said person needing such treatment.

50. A method of treating back pain according to claim 49 wherein said skin temperature is maintained at a temperature of from about 32° C. to about 41° C. for a time period of greater than about 4 hours, wherein said relief of said pain is substantially prolonged for at least about 1 day after removal of said heat from the back of said person needing such treatment.

51. A method of treating back pain, selected from the group consisting of acute muscular, acute skeletal, acute referred, recurrent muscular, recurrent skeletal, recurrent referred, chronic muscular, chronic skeletal, and chronic referred back pain, by applying a disposable thermal back wrap of claim 24 to the back of a person needing such treatment, to maintain a skin temperature to the back of from about 32° C. to about 50° C. for a time period of from about twenty seconds to about twenty-four hours, wherein said skin temperature and said period of time of maintaining said skin temperature is appropriately selected by said person needing such treatment, to substantially relieve said pain without adverse events.

52. A method of treating back pain according to claim 51 wherein said skin temperature is maintained from about 32° C. to about 39° C.

53. A method of treating back pain according to claim 51 wherein said skin temperature is maintained at a temperature of from about 32° C. to about 43° C. for a time period of greater than about 1 hour, wherein said relief of said pain is substantially prolonged for at least about 2 hours after removal of said heat from the back of said person needing such treatment.

54. A method of treating back pain according to claim 53 wherein said skin temperature is maintained at a temperature of from about 32° C. to about 41° C. for a time period of greater than about 4 hours, wherein said relief of said pain is substantially prolonged for at least about 1 day after removal of said heat from the back of said person needing such treatment.

* * * * *